United States Patent
Ohto et al.

(10) Patent No.: US 8,173,435 B2
(45) Date of Patent: May 8, 2012

(54) METHOD FOR EVALUATING OIL-AND-FAT AMOUNT IN SEED AND METHOD FOR SCREENING FOR PLANT EXHIBITING VARIED LEVEL OF OIL-AND-FAT CONTENT

(75) Inventors: Chikara Ohto, Toyota (JP); Norihiro Mitsukawa, Miyoshi (JP); Makoto Hayashi, Toyohashi (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 57 days.

(21) Appl. No.: 12/920,098

(22) PCT Filed: Feb. 23, 2009

(86) PCT No.: PCT/JP2009/053782
§ 371 (c)(1),
(2), (4) Date: Aug. 27, 2010

(87) PCT Pub. No.: WO2009/107820
PCT Pub. Date: Sep. 3, 2009

(65) Prior Publication Data
US 2011/0006221 A1    Jan. 13, 2011

(30) Foreign Application Priority Data
Feb. 28, 2008   (JP) .................... 2008-048485

(51) Int. Cl.
*G01N 33/03* (2006.01)
*G01N 33/92* (2006.01)

(52) U.S. Cl. .............. 436/71; 436/20; 436/63; 436/172

(58) Field of Classification Search .............. 436/20, 436/63, 71, 86, 172
See application file for complete search history.

(56) References Cited

U.S. PATENT DOCUMENTS

| | | | |
|---|---|---|---|
| 5,977,436 A * | 11/1999 | Thomas et al. | 800/281 |
| 2004/0205844 A1 * | 10/2004 | Moloney et al. | 800/281 |
| 2005/0172359 A1 | 8/2005 | Moloney et al. | |
| 2007/0006343 A1 * | 1/2007 | Moloney et al. | 800/281 |
| 2008/0104725 A1 | 5/2008 | Siloto et al. | |
| 2008/0216198 A1 * | 9/2008 | Zhao et al. | 800/290 |
| 2009/0203093 A1 * | 8/2009 | Steinbuchel et al. | 435/134 |
| 2011/0263487 A1 * | 10/2011 | Meagher | 514/4.5 |

FOREIGN PATENT DOCUMENTS

JP   2007-510420 A   4/2007

(Continued)

OTHER PUBLICATIONS

Wahlroos, T. et al, Plant Physiology and Biochemistry 2003, 41, 773-778.*

(Continued)

*Primary Examiner* — Arlen Soderquist
(74) *Attorney, Agent, or Firm* — Sughrue Mion, PLLC (57) ABSTRACT

This invention is intended to evaluate the oil-and-fat amount in a seed and genetic changes thereof. A fusion protein of an oil body-specific protein, such as the oleosin-GFP fusion protein, and a fluorescent protein is expressed, and the oil-and-fat amount in a plant seed and changes thereof are evaluated based on the fluorescent intensity in a cotyledon of a fluorescent protein, such as GFP.

29 Claims, 2 Drawing Sheets
(1 of 2 Drawing Sheet(s) Filed in Color)

FOREIGN PATENT DOCUMENTS

JP         2008-515406 A      5/2008

OTHER PUBLICATIONS

Pol, A. et al, Molecular Biology of the Cell 2004, 15, 99-110.*
Vandana, S. et al, Plant Physiology and Biochemistry 2006,44,714-723.*
Yonghua Li, et al., "Oil content of *Arabidopsis* seeds: The influence of seed anatomy, light and plant-to-plant variation," Phytochemistry, 2006, vol. 67, No. 9, pp. 904-915.
Jason T. C. Tzen, et al., "Lipids, Proteins, and Structure of Seed Oil Bodies from Diverse Species," Plant Physiology, 1993, vol. 101, pp. 267-276.
Rodrigo M.P. Siloto, et al., "The Accumulation of Oleosins Determines the Size of Seed Oilbodies in *Arabidopsis*," The Plant Cell, Aug. 2006, pp. 1961-1974, vol. 18, No. 8.
Julie T.L. Ting, et al., "Olesin genes in maize kernels having diverse oil contents are constitutively expressed independent of oil contents," Planta, 1996, pp. 158-165, vol. 199, No. 1.
[Chapter 3: Method for observing architecture and function of intracellular structure, Structure and function of oil body] Dai 3 sho saibonai kozo no Kochiku to Kino no Kansatsuho Oil Body no Kozo to Kino, Saibo Kogaku Bessatsu Shokubutsu Saibo Kogaku Series 22 New Edition Shokubutsu no Saibo O Miru Jikken Protocol, Apr. 3, 2006, pp. 219-220, 2nd Edition, 1st Print, Shujunsha Co., Ltd.
Tony Wahlroos, et al., "Olesin Expression and Trafficking During Oil Body Biogenesis in Tobacco Leaf Cells," Genesis, 2003, pp. 125-132, vol. 35, No. 2.
Wan-ling Chiu, et al., "Engineered GFP as a vital reporter in plants," Current Biology (Research Paper), 1996, pp. 325-330, vol. 6, No. 3.
D.J. Murphy, et al., "The biogenesis and funtions of lipid bodies in animals, plants and microorganisms," Progress in Lipid Research, 2001, pp. 325-438, vol. 40.
Jonathan A.Napier, et al., "The structure and biogenesis of plant oil bodies: the role of the ER membrane and the oleosin class of proteins," Plant Molecular Biology, 1996, pp. 945-956, vol. 31.
Yasuo Niwa, "A Synthetic Green Fluorescent Protein Gene for Plant Biotechnology," Plant Biotechnology (Review), 2003, pp. 1-11, vol. 20, No. 1.
Chi-Chung Peng, et al., "A system for purification of recombinant proteins in *Escherichia coli* via artificial oil bodies constituted with their oleosin-fused polypeptides," Journal of Biotechnology, 2004, pp. 51-57, vol. 111.
Chi-Chung Peng, et al., "Size and Stability of Reconstituted Sesame Oil Bodies," Biotechnol. Prog., 2003, pp. 1623-1626, vol. 19.
Zita Purkrtova, et al., "Structure and function of seed lipid body-associated proteins," C. R. Biologies, 2008, pp. 746-754, vol. 331.
Jen Sheen, et al., "Green-fluorescent protein as a new vital marker in plant cells," The Plant Journal, 1995, pp. 777-784, vol. 8, No. 5.
Gijs J.H. Van Rooijen, et al., "Nucleotide sequence of an *Arabidopsis thaliana* oleosin gene," Plant Molecular Biology, 1992, pp. 1177-1179, vol. 18.
Dagmar Zweytick, et al., "Intracellular lipid particles of eukaryotic cells," Biochemica et Biophysica Acta, 2000, pp. 101-120, vol. 2000.

* cited by examiner

METHOD FOR EVALUATING OIL-AND-FAT AMOUNT IN SEED AND METHOD FOR SCREENING FOR PLANT EXHIBITING VARIED LEVEL OF OIL-AND-FAT CONTENT

CROSS REFERENCE TO RELATED APPLICATIONS

This application is a National Stage of International Application No. PCT/JP2009/053782 filed Feb. 23, 2009, which claims priority from Japanese Patent Application No. 2008-048485, filed Feb. 28, 2008, the contents of all of which are incorporated herein by reference in their entirety.

TECHNICAL FIELD

The present invention relates to a method for evaluating the oil-and-fat amount in a seed and a method for screening for a plant exhibiting a varied level of oil-and-fat content.

BACKGROUND ART

Oil bodies (occasionally referred to as "lipid bodies") are cell organelles that are present in large quantities in plants, and particularly in seed cells of oil crops. Oil bodies comprise a monolayer membrane of phospholipid comprising specific proteins referred to as oleosins, steroleosins, and caleosins, and they accumulate plant oil-and-fats in the form of triacylglycerol (TAG, neutral fat, or neutral lipid) therein. In particular, large quantities of plant oil-and-fats are accumulated in plant seeds. In the past, oil-and-fats accumulated in oil bodies have been analyzed by methods that involve pulverizing seeds to extract oil-and-fat components and performing gas chromatography, liquid chromatography, or other techniques. Such analytical methods, however, required the addition of lipid degradation inhibitors and processing at low temperatures. In addition, oil-and-fat components may be disadvantageously degraded.

Siloto, R. M. P. et al., Plant Cell 18, 1961-1974, 2006 discloses that oil body size is influenced by oleosin quantity. Wahlroos et al., GENESIS, 35 (2): 125-132, 2003 discloses that the oleosin gene is fused to the green fluorescent protein (GFP) gene and oil bodies, which are organelles in plant cells, can be observed with the aid of GFP fluorescence. Even if it is possible to observe oil bodies, however, the correlation between the number or form of oil bodies and the oil-and-fat amount or type accumulated in oil bodies has not yet been elucidated. In particular, the correlation between the form or number of oil bodies in cotyledons and the oil-and-fat amount in seeds has not yet been elucidated. During the growth process, a variety of reserved compounds, such as reserved starches, reserved proteins, and reserved oil-and-fats, are degraded and used in cotyledons while undergoing photosynthesis. Thus, it was considered to be difficult to deduce the oil-and-fat amount in seeds based on the form or number of oil bodies in cotyledons.

DISCLOSURE OF THE INVENTION

Under the above-described circumstances, the present invention is intended to evaluate the oil-and-fat amount in a seed in a nondestructive manner and to screen for a mutant plant exhibiting a varied level of oil-and-fat amount in a seed via nondestructive evaluation of changes in the oil-and-fat amount in a seed.

The present inventors have conducted concentrated studies in order to attain the above objects, expressed an oleosin-GFP fusion protein, and discovered that the oil-and-fat amount in a plant seed could be evaluated based on the GFP fluorescence intensity, thereby completing the present invention.

Specifically, the present invention includes the following.

(1) A method for evaluating the oil-and-fat amount in a seed comprising a step of measuring the visible light intensity in a cotyledon of a plant that expresses a fusion protein of a protein that has oil body specificity and a protein that can be detected by visible light and a step of evaluating the oil-and-fat content in a seed based on the visible light intensity measured in the former step.

(2) The method for evaluation according to (1), wherein the protein that has oil body specificity is a protein selected from the group consisting of oleosin, steroleosin, and caleosin.

(3) The method for evaluation according to (1), wherein the protein that has oil body specificity is oleosin.

(4) The method for evaluation according to (1), wherein the protein that can be detected by visible light is green fluorescent protein (GFP).

(5) The method for evaluation according to (1), wherein the step of evaluating the oil-and-fat content comprises calculating the sum of visible light intensities in a cotyledon and conducting an evaluation based on a positive correlation between the sum and the oil-and-fat content in a seed.

(6) The method for evaluation according to (5), which further comprises a step of evaluating the positive correlation between the sum of visible light intensities and the oil-and-fat content in a seed based on measured values obtained via a measurement of the sum of visible light intensities and quantification of the oil-and-fat content in unpulverized seeds using pulsed NMR.

(7) The method for evaluation according to (6), wherein the measurement of the sum of visible light intensities is carried out with the use of a fluorescence microscope, a fluorospectrophotometer, a fluorescent titer plate reader, or a fluorescent image analyzer.

(8) The method for evaluation according to (1), wherein the plant is obtained from a plant cell or a cultured plant cell that has been subjected to mutagen treatment.

(9) The method for evaluation according to (1), wherein the plant is an oil plant.

(10) The method for evaluation according to (1), wherein the plant is a dicotyledonous plant.

(11) The method for evaluation according to (1), wherein the plant belongs to the genus Brassicaceae.

(12) The method for evaluation according to (1), wherein the plant is *Arabidopsis thaliana*.

(13) The method for evaluation according to (1), wherein the visible light intensities are measured with the use of a fluorescent microscope, a fluorospectrophotometer, a fluorescent titer plate reader, or a fluorescent image analyzer.

(14) A method of screening a plant species, a plant variety, or a mutant plant exhibiting a varied level of oil-and-fat content in a seed comprising a step of measuring visible light intensities in a cotyledon of a plant cell, a cultured plant cell, or a plant that expresses a fusion protein of a protein that has oil body specificity and a protein that can be detected by visible light.

(15) The method for screening according to (14), wherein the protein that has oil body specificity is a protein selected from the group consisting of oleosin, steroleosin, and caleosin.

(16) The method for screening according to (14), wherein the protein that has oil body specificity is oleosin.

(17) The method for screening according to (14), wherein the protein that can be detected by visible light is green fluorescent protein (GFP).

(18) A method for screening for a plant exhibiting a varied level of oil-and-fat content comprising a step of subjecting a plant cell, a cultured plant cell, or a plant expressing a fusion protein of a protein that has oil body specificity and a protein that can be detected by visible light to mutagen treatment, a step of measuring visible light intensities in a cotyledon after the step of mutagen treatment, and a step of evaluating changes in the oil-and-fat content in a seed resulting from the mutagen treatment based on the visible light intensities measured in the above step.

(19) The method for screening according to (18), wherein the protein that has oil body specificity is a protein selected from the group consisting of oleosin, steroleosin, and caleosin.

(20) The method for screening according to (18), wherein the protein that has oil body specificity is oleosin.

(21) The method for screening according to (18), wherein the protein that can be detected by visible light is green fluorescent protein (GFP).

(22) The method for screening according to (19), wherein the step of evaluating changes in the oil-and-fat content comprises calculating the sum of visible light intensities in a cotyledon and conducting an evaluation based on a positive correlation between the sum and the oil-and-fat content in a seed.

(23) The method for screening according to (22), which further comprises a step of evaluating the positive correlation between the sum of visible light intensities and the oil-and-fat content in a seed based on measured values obtained via a measurement of the sum of visible light intensities and quantification of the oil-and-fat content in unpulverized seeds using pulsed NMR.

(24) The method for screening according to (23), wherein the measurement of the sum of visible light intensities is carried out with the use of a fluorescence microscope, a fluorospectrophotometer, a fluorescent titer plate reader, or a fluorescent image analyzer.

(25) The method for screening according to (18), wherein the plant is an oil plant.

(26) The method for screening according to (18), wherein the plant is a dicotyledonous plant.

(27) The method for screening according to (18), wherein the plant belongs to the genus Brassicaceae.

(28) The method for screening according to (18), wherein the plant is *Arabidopsis thaliana*.

(29) The method for screening according to (18), wherein the visible light intensities are measured with the use of a fluorescent microscope, a fluorospectrophotometer, a fluorescent titer plate reader, or a fluorescent image analyzer.

This description includes part or all of the contents as disclosed in the description and/or drawings of Japanese Patent Application No. 2008-048485, which is a priority document of the present application.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A schematically shows the constitution of the oleosin-GFP fusion gene, and FIGS. 1B to 1D each show a fluorescence picture of cotyledons of OleG, mutant A, and mutant B 6 days after the initiation of germination in the dark.

BEST MODES FOR CARRYING OUT THE INVENTION

Hereafter, the present invention is described in detail with reference to the drawings.

In the present invention, the oleosin-GFP fusion gene was used to transform a model plant *Arabidopsis thaliana*, and oil bodies contained in the cotyledons obtained from the transgenic *Arabidopsis thaliana* plant were fluorescently visualized. Specifically, the sampled seeds were allowed to germinate, and fluorescence in the developed cotyledons was observed, thereby observing oil bodies contained in the seeds. A mutation was induced (i.e., mutagen treatment was performed) in such transgenic *Arabidopsis thaliana* plant, changes in various properties, such as the configuration and the number of oil bodies, were observed, and changes in the oil-and-fat content and oil compositions were measured. Among various properties of oil bodies, surprisingly, a positive correlation was found between the sum of fluorescent intensities in cotyledons (i.e., fluorescence intensity per unit area) and the oil-and-fat content in a seed.

Based on such finding, it was found that the oil-and-fat content in a plant seed and changes thereof could be measured and evaluated by measuring the visible light intensities in cotyledons of a plant that expresses a gene encoding a fusion protein of a protein that has oil body specificity and a protein that can be detected by visible light. The method for evaluation according to the present invention is based on such finding and this method is intended to quantitatively evaluate the oil-and-fat amount in a seed. Also, the screening method according to the present invention is based on such finding and this method is intended to screen for a mutant plant exhibiting a genetically varied level of oil-and-fat amount in a seed due to mutagen treatment. This screening method is effective when the oil-and-fat amount in a seed is genetically varied, and such method is applicable to plant species and plant varieties exhibiting varied levels of oil-and-fat amounts in seeds, in addition to mutant plants.

In the present invention, a plant that expresses a fusion protein of a protein that has oil body specificity and a protein that can be detected by visible light is first prepared. Examples of proteins that are present in an oil body-specific manner include membrane proteins, such as oleosin, steroleosin, and caleosin. A fusion protein may comprise one or a plurality of types of such membrane proteins. Examples of proteins that can be detected by visible light include a fluorescent protein and a photoprotein. Fluorescent proteins that can be used are not limited to the green fluorescent protein (GFP), and various GFP mutant proteins that are known to have the effects similar to those of GFP (e.g., YFP (yellow fluorescent protein), RFP (red fluorescent protein), OFP (orange fluorescent protein), and BFP (blue fluorescent protein)) and other fluorescent proteins can be used. An example of a photoprotein is luciferase. Use of the aforementioned fluorescent protein as a protein that can be detected by visible light is particularly preferable because a fluorescent protein can be quantitatively analyzed via a conventional fluorescence assay technique with very high accuracy. Hereafter, the fusion protein of oleosin and GFP (it is hereafter noted as "the oleosin-GFP fusion protein") is described as a representative example; however, it is apparent that the fusion protein is not limited to the oleosin-GFP fusion protein.

The oleosin-GFP fusion protein can be expressed in a plant of interest by obtaining a fusion gene that encodes such fusion protein via a conventional genetic engineering technique. As examples, the nucleotide sequence of the fusion gene encoding the oleosin-GFP fusion protein and the amino acid sequence of the oleosin-GFP fusion protein are shown in SEQ ID NOs: 1 and 2, respectively.

In the present invention, the oleosin-GFP fusion protein is not limited to a protein comprising the amino acid sequence as shown in SEQ ID NO: 2, and it may be a protein comprising an amino acid sequence derived from the amino acid sequence as shown in SEQ ID NO: 2 by deletion, substitution, addition, or insertion of 1 or a plurality of amino acid residues, existing in an oil body membrane, and emitting fluorescence. The term "a plurality of amino acids" used herein refers to 2 to 40, preferably 2 to 30, more preferably 2 to 20, further preferably 2 to 10, and most preferably 2 to 5 amino acids.

The oleosin-GFP fusion protein may be a protein having 70% or higher homology to the amino acid sequence as shown in SEQ ID NO: 2. Such homology is preferably 80% or higher, more preferably 85% or higher, further preferably 90% or higher, and most preferably 95% or higher.

Deletion, addition, or substitution of amino acids can be realized by modifying a gene encoding the above-mentioned protein via a method known in the art. A mutation can be introduced into a gene via known methods, such as the Kunkel or gapped duplex method, or methods in accordance therewith. For example, a mutation is introduced with the use of mutagenesis kits utilizing site-directed mutagenesis (e.g., Mutant-K or Mutant-G (manufactured by Takara Bio Inc.)) or the LA PCR in vitro Mutagenesis Series Kit (manufactured by Takara Bio Inc.). A mutation may be introduced into the gene via a method involving the use of chemical mutagens typified by EMS (ethyl methane sulfonate), 5-bromouracil, 2-aminopurine, hydroxylamine, N-methyl-N'-nitro-N-nitrosoguanidine, or other carcinogenic compounds, radiation processing typified by the use of x-rays, alpha rays, beta rays, gamma rays, or ion beams, or ultrasonic processing.

Further, the gene encoding the oleosin-GFP fusion protein comprises DNA hybridizing under stringent conditions to DNA comprising a nucleotide sequence complementary to the nucleotide sequence as shown in SEQ ID NO: 1 and encoding a protein existing in an oil body membrane and emitting fluorescence. Under stringent conditions, so-called specific hybrids are formed, but non-specific hybrids are not formed. For example, hybridization is carried out at 45° C. in the presence of 6×SSC (sodium chloride/sodium citrate), followed by washing at 50° C. to 65° C. in the presence of 0.2 to 1×SSC and 0.1% SDS. Alternatively, hybridization is carried out at 65° C. to 70° C. in the presence of 1×SSC, followed by washing at 65° C. to 70° C. in the presence of 0.3×SSC.

When the nucleotide sequence of the gene encoding the oleosin-GFP fusion protein is identified, such gene can be obtained from a variety of plants via chemical synthesis, PCR using the cloned cDNA template, or hybridization using the DNA fragment having the nucleotide sequence of interest as a probe.

The gene encoding the oleosin-GFP fusion protein of the present invention described above is functionally expressed in a plant of interest via modification involving substitution of the wild-type oleosin gene in the plant genome. In the present invention, alternatively, the gene encoding the fusion protein may be introduced into a plant lacking the wild-type oleosin gene in the plant genome, so that such gene is expressed. Further, the gene encoding the fusion protein of the present invention may be introduced, so that such gene is overexpressed without lacking the wild-type oleosin in the plant genome.

Examples of vectors that can be preferably used for introducing and expressing the gene encoding the oleosin-GFP fusion protein in a plant cell include pBI vectors, pUC vectors, and pTRA vectors. pBI and pTRA vectors can introduce a target gene into a plant with the use of *Agrobacterium*. pBI binary vectors or intermediate vectors are preferably used, and examples thereof include pBI121, pBI101, pBI101.2, and pBI101.3. pUC vectors can directly introduce a gene into a plant, and examples thereof include pUC18, pUC19, and pUC9. Also, plant virus vectors, such as cauliflower mosaic virus (CaMV), bean golden mosaic virus (BGMV), and tobacco mosaic virus (TMV) vectors, can be used.

It is necessary that the gene encoding the oleosin-GFP fusion protein is incorporated into a vector, so that the functions of such gene are exhibited. Accordingly, a promoter and, according to need, an enhancer, a splicing signal, a poly A addition signal, a selection marker, a 5'-UTR sequence, or the like can be ligated to the vector. Examples of selection markers include the dihydrofolate reductase gene, the ampicillin resistance gene, the neomycin resistance gene, the hygromycin resistance gene, and the bialaphos resistance gene.

As the "promoter," DNA may not be derived from a plant, provided that such DNA can function in a plant cell and induce expression in a given tissue or at a given growth phase of the plant. Specific examples include 35S promoters of cauliflower mosaic virus (CaMV), promoters of nopaline synthase genes (Pnos), maize ubiquitin promoters, rice actin promoters, and tobacco PR protein promoters.

Any sequence may be used as the "terminator," provided that such sequence can terminate the transcription of the gene transcribed by the promoter. Specific examples include terminators of noparine synthase genes (Tnos) and cauliflower mosaic virus poly A terminators.

An "enhancer" is used for improving the expression efficiency of a target gene. For example, an enhancer region including a sequence located upstream in the CaMV35S promoter is preferable.

A transgenic plant can be prepared in accordance with a conventional technique using an expression vector having the gene encoding the oleosin-GFP fusion protein. A transgenic plant can be obtained by introducing such expression vector into a host cell, so that the introduced gene can be expressed therein. Targets of transformation are plant tissues (including the epidermis, the phloem, the parenchyma, the xylem, the vascular bundle, and the plant organs (e.g., leaves, petals, stems, radicals, and seeds)) or plant cells.

Examples of plants that are used for transformation include, but are not limited to, dicotyledonous plants and monocotyledonous plants, such as plants of Brassicaceae, Gramineae, Solanaceae, Leguminosae, and Salicaceae (see below).

Examples of Brassicaceae plants include *Arabidopsis thaliana*, oilseed rape (*Brassica rapa* and *Brassica napus*), cabbage (*Brassica oleracea* var. *capitata*), rapeseed (*Brassica rapa* and *Brassica napus*), field mustard (*Brassica rapa* and *Brassica napus*), *Brassica pekinensis* (*Brassica rapa* var. *pekinensis*), bok Choy (*Brassica rapa* var. *chinensis*), turnip (*Brassica rapa* var. *rapa*), *Brassica rapa* var. *hakabura*, *Brassica rapa* var. *lancinifolia*, *Brassica rapa* var. *peruviridis*, pak Choi (*Brassica rapa* var. *chinensis*), Japanese radish (*Brassica Raphanus sativus*), and horseradish (*Wasabia japonica*).

Examples of Solanaceae plants include tobacco plants (*Nicotiana tabacum*), eggplants (*Solanum melongena*), potatoes (*Solaneum tuberosum*), tomatoes (*Lycopersicon lycopersicum*), capsicum (*Capsicum annuum*), and Petunia.

Examples of Leguminosae plants include soybeans (*Glycine max*), peas (*Pisum sativum*), horse beans (*Vicia faba*), *Wisteria floribunda*, peanuts (*Arachis. hypogaea*), bird's-foot trefoils (*Lotus corniculatus* var. *japonicus*), bush beans (*Phaseolus vulgaris*), azuki beans (*Vigna angularis*), and *Acacia*.

Examples of Compositae plants include Chrysanthemums (*Chrysanthemum morifolium*) and sunflowers (*Helianthus annuus*).

Examples of Arecaceae plants include *Elaeis guineensis* (or *Elaeis oleifera*), *Cocos nucifera*, *Phoenix dactylifera*, and *Copernicia*.

Examples of Anacardiaceae plants include *Rhus succedanea*, *Anacardium occidentals*, *Toxicodendron vernicifluum*, *Mangifera indica*, and pistachio (*Pistacia vera*).

Examples of Cucurbitaceae plants include pumpkins (*Cucurbita maxima*, *Cucurbita moschata*, or *Cucurbita pepo*), cucumbers (*Cucumis sativus*), *Trichosanthes cucumeroides*, and gourds (*Lagenaria siceraria* var. *gourda*).

Examples of Rosaceae plants include almonds (*Amygdalus communis*), roses (*Rosa*), strawberries (*Fragaria*), cherry trees (*Prunus*), and apples (*Malus pumila* var. *domestica*).

Examples of Caryophyllaceae plants include carnations (*Dianthus caryophyllus*).

Examples of Salicaceae plants include *Populus nigra* (*Populus trichocarpa*, *Populus nigra*, or *Populus tremula*).

Examples of Gramineae plants include maize (*Zea mays*), rice (*Oryza sativa*), barley (*Hordeum vulgare*), wheat (*Triticum aestivum*), bamboo (*Phyllostachys*), and sugarcane (*Saccharum officinarum*).

Examples of Liliaceae plants include tulips (*Tulipa*) and lilies (*Lilium*).

Examples of methods for introducing an expression vector or a DNA fragment having the gene encoding the oleosin-GFP fusion protein into a plant include the *Agrobacterium* method, the PEG-calcium phosphate method, the electroporation method, the liposome method, the particle gun method (the bombardment method), and the microinjection method. When the *Agrobacterium* method is employed, for example, protoplasts or tissue sections are used. When protoplasts are used, protoplasts may be subjected to coculture with *Agrobacterium* having Ti plasmids or may be fused to *Agrobacterium* spheroplasts (i.e., the spheroplast method). When tissue sections are used, tissue sections may be infected with an aseptically-cultured leaf disc of a target plant via a leaf disk (the leaf disc method), tissue sections may be infected with calluses (undifferentiated cultured cells), or the tissue sections may directly infiltrate flower tissue. When transforming monocotyledonous plants by the *Agrobacterium* method, acetosyringone can be used to enhance the efficiency of transformation.

Whether or not the gene encoding the oleosin-GFP fusion protein has been incorporated into a plant can be confirmed via PCR, Southern hybridization, Northern hybridization, or other techniques. For example, DNA is prepared from a transgenic plant, DNA-specific primers are designed, and PCR is carried out. After PCR is performed, the amplification product may be subjected to agarose gel electrophoresis, polyacrylamide gel electrophoresis, or capillary electrophoresis, the resultant is stained with ethidium bromide, SYBR Green, or the like, and the amplification product is detected as a band. Thus, transformation can be confirmed. Alternatively, PCR may be carried out with the use of primers that have been labeled with fluorescent dyes or the like in advance, and the amplification product can be detected. Further, the amplification product may be bound to a solid phase, such as a microplate, and the amplification product may be detected via fluorescent, enzyme, or other reactions.

As a result of transformation, the resulting tumor tissues, shoots, capillary roots, seeds, or the like can be used for cell culture, tissue culture, or organ culture in that state. Alternatively, conventional plant tissue culture techniques may be employed to reproduce plants therefrom via administration of plant hormones (e.g., auxin, cytokinine, gibberellin, abscisic acid, ethylene, or brassinoride) at adequate concentrations. In general, plants are reproduced from the cultured cell by differentiating the radicals on a medium containing a mixture of adequate types of auxin and cytokinine, transferring the resultants to a medium containing a larger quantity of cytokinine to differentiate shoots, and transferring the resultants to hormone-free soils.

Thus, a transgenic plant into which the gene encoding the oleosin-GFP fusion protein has been introduced can be prepared. In the resulting transgenic plant, the oleosin-GFP fusion protein is expressed in an oil body membrane, and an oil body can be visualized by observing fluorescence derived from a fluorescent protein, such as GFP.

In the present invention, fluorescence intensity in a cotyledon of a plant expressing the oleosin-GFP fusion protein is then measured. Specifically, the seeds sampled from the thus-prepared transgenic plant are allowed to germinate, and fluorescence intensity in the developed cotyledon is measured. Means and apparatuses used for measuring fluorescence intensity are not particularly limited, and examples include a fluorescent microscope, a fluorospectrophotometer, a fluorescent titer plate reader, and a fluorescent image analyzer.

As the fluorescence intensity in the cotyledon, a sum of fluorescence intensities observed in the cotyledon is calculated. Specifically, it can be calculated as the sum of fluorescence intensity of the image (i.e., a=sum; fluorescence intensity×pixel number). The fluorescence intensity and the pixel number having relevant fluorescence intensity are determined based on a confocal image obtained under the same condition in the same area with the same pixel number.

The oil-and-fat amount in a seed can be evaluated based on a sum of fluorescence intensities thus determined. Specifically, the sum of fluorescence intensities derived from a fluorescent protein, such as GFP, in a cotyledon is positively correlated with the oil-and-fat amount in a seed. This enables evaluation of the oil-and-fat amount in a seed based on the sum of fluorescence intensities derived from a fluorescent protein, such as GFP, in a cotyledon. More specifically, the sum of fluorescence intensities in a cotyledon of a plant regenerated from a plant cell or a cultured plant cell, which had been subjected to mutagen treatment, is determined, and the obtained value is compared with a sum of fluorescence intensities in a cotyledon of an untreated plant. If the sum of fluorescence intensities in a cotyledon of a plant, which had been subjected to mutagen treatment, is significantly increased compared with the sum of fluorescence intensities in a cotyledon of an untreated plant consequently, it indicates that a mutation of increasing the oil-and-fat amount in a seed is introduced via mutagen treatment. Thus, determination of the sum of fluorescence intensities in a cotyledon of a plant resulting from mutagen treatment enables screening of a mutant plant exhibiting an increased level of oil-and-fat amount in a seed. If the sum of fluorescence intensities in a cotyledon of a plant resulting from mutagen treatment is significantly decreased compared with the sum of fluorescence intensities in a cotyledon of an untreated plant, however, it indicates that a mutation of decreasing the oil-and-fat amount in a seed is introduced via mutagen treatment. Thus, determination of the sum of fluorescence intensities in a cotyledon of a plant resulting from mutagen treatment enables screening of a mutant plant exhibiting a decreased level of oil-and-fat amount in a seed.

Mutagen treatment is not particularly limited, and treatment with the use of a chemical mutagen and/or physical mutagen that is extensively employed for mutagenesis can be performed. Examples of chemical mutagens that can be used include ethyl methane sulfonate (EMS), ethylnitrosourea (ENS), 2-aminopurine, 5-bromouracil (5-BU), and an alkylating agent. Also, radioactive rays, ultraviolet ray, and the like can be used as physical mutagens. Mutagenesis with the use of such mutagens can be carried out via a conventional technique.

Targets of evaluation of the oil-and-fat amount in a seed are not limited to mutant plants resulting from mutagen treatment, and different plant species and plant varieties can also be targets.

The oil-and-fat amount in a seed is the most critical phenotype in oil crops, such as rapeseed, soybean, sunflower, and oil palm. A phenotype such as the oil-and-fat amount in a seed is a so-called quantitative phenotype, which is intricately influenced by complicated genotypes. According to the evaluation method and the screening method of the present invention, the oil-and-fat amount in a seed and changes thereof can be evaluated in a simple manner with a high throughput, without the need for laborious steps of destruction of seeds, extraction and purification of oil-and-fat components therefrom, and quantitative analysis thereof.

Hereafter, the present invention is described in greater detail with reference to the examples, although the technical scope of the present invention is not limited to the following examples.

Example 1

In this example, *Arabidopsis thaliana* plants that are extensively used as model plants were transformed so as to express an oleosin-GFP fusion gene, and transgenic plants in which oil bodies can be observed with the aid of fluorescence were prepared. Thereafter, the resulting transgenic plants were subjected to mutation, and mutants exhibiting varied oil-and-fat amounts in seeds were identified using changes in oil body properties as an indicator. Hereafter, the concrete process of experiment and the results of experiment are described in detail.

Material and Method
<Plant Material>

The *Arabidopsis thaliana* ecotype Columbia was used. In accordance with a conventional technique, plants were subjected to seed sterilization and germination in sterile agar medium (½ Murashige and Skoog medium, 0.8% agar) for 7 days at 22° C. under light. Thereafter, plants were planted in a pot containing vermiculite and pearlite (1:1) and grown at 22° C. for 16 hours under light and for 8 hours in the dark.
<Preparation of Oleosin-GFP Gene>

RNA was isolated from the sheath of *Arabidopsis thaliana* using an RNeasy plant mini kit (Quiagen) and subjected to reverse transcription using the SuperScript III first strand synthesis system for RT-PCR (Invitrogen). PCR was carried out using the obtained cDNA, primer 1 ($^3$'AAAAAGCAGCTCAATGGCGGATACAGCTAGAGGA$^3$': SEQ ID NO: 3), and primer 2 ($^3$'CTCGCCCTTGCTCACCATAGTAGTGTGCTGGCCACC$^3$': SEQ ID NO: 4), and DNA fragment A having part of the attB1 sequence and part of the GFP gene at both ends of oleosin S3 cDNA was amplified. Separately, PCR was carried out using cDNA encoding the green fluorescent protein (GFP) from Aequorea victoria, primer 3 ($^3$'GGTGGCCAGCACACTACTATGGTGAGCAAGGGCGAG$^3$': SEQ ID NO: 5), and primer 4 ($^3$'AGAAAGCTGGGTCTTACTTGTACAGCTCGTCCAT$^3$': SEQ ID NO: 6), and DNA fragment B having part of oleosin S3 cDNA and part of the attB2 sequence added to both ends of GFP cDNA was amplified. Subsequently, DNA fragment A, DNA fragment B, primer 5 ($^3$'GGGG ACA AGT TTG TAC AAA AAA GCA GGC T$^3$': SEQ ID NO: 7), and primer 6 ($^3$'GGGG AC CAC TTT GTA CAA GAA AGC TGG G$^3$': SEQ ID NO: 8) were mixed, and PCR was further carried out to prepare an oleosin-GFP fusion gene having the attB1 sequence and the attB2 sequence at both ends. The nucleotide sequence of the oleosin-GFP fusion gene and the amino acid sequence of the gene product are shown in SEQ ID NOs: 1 and 2.

The obtained fusion gene was cloned into a Ti vector having the attR1 and attR2 sequences downstream of the CaMV 35S promoter and having a kanamycin-resistant marker with the aid of the pDONR221 vector in accordance with the protocol of the Gateway system (Invitrogen). The obtained plasmid was introduced into *Agrobacterium* (*Agrobacterium tumefacience* C58C1 rifR) via electroporation, and the resultant was designated as Ti-OleG.
<Transformation into *Arabidopsis thaliana*>

The oleosin-GFP fusion gene was introduced into the genome of *Arabidopsis thaliana* by the *Agrobacterium* method. At the outset, Ti-OleG was allowed to grow in YEB medium (5 g/l polypeptone, 5 g/l beef extract, 1 g/l yeast extract, 5 g/l sucrose, 0.5 g/l MgSO$_4$) until the absorbance at 600 nm (A600) reached 0.8 to 1.0 at 28° C., and it was then harvested via centrifugation. The resulting cells were suspended in an infiltration solution (10 mM MgCl$_2$, 5% sucrose, 0.05% Silwet L-77) so as to adjust A600 at 0.8. After scapes of flowering *Arabidopsis thaliana* were soaked in the suspension for 1 minute, fructified seeds were collected. The collected seeds were sterilized and then sowed in sterile agar medium containing 25 mgm/l kanamycin, and the transgenic *Arabidopsis thaliana* plant into the genome of which the oleosin-GFP fusion gene had been inserted was isolated using kanamycin resistance as an indicator. Seeds were obtained from the resulting transgenic *Arabidopsis thaliana* plant, and progenies of the transgenic plants, which were homozygous for the kanamycin resistance marker, were selected and designated as OleG.
<Transgenic Plant Mutagen Treatment>

OleG seeds were treated with a 0.2% ethyl methane sulfonate solution for 16 hours and then sowed in a pot containing vermiculite and pearlite (1:1). The seeds were grown at 22° C. under light for 16 hours and in the dark for 8 hours, and the progeny seeds were collected and designated as M2 seeds.
<GFP Fluorescence Observation>

Mutants were screened for using a fluorescence stereomicroscope (Carl Zeiss SteREO Lumar V12). The OleG and M2 seeds were vertically positioned on sterile agar medium and germinated in the dark for 6 days. The GFP fluorescence of the oleosin-GFP fusion protein in cells of etiolated cotyledons, embryonic axes, and radicals was observed under a fluorescence stereomicroscope (Carl Zeiss). Seeds having GFP fluorescence intensities and distributions different from those of OleG were identified as mutants.

In order to compare GFP fluorescence of the oleosin-GFP fusion protein of the OleG and mutant seeds, a confocal laser microscope (Carl Zeiss LSM 510) was used. Etiolated cotyledons, embryonic axes, and radicals were cut from the OleG and mutant seeds, which had been germinated in the dark for 6 days, and they were then mounted on a glass slide. GFP fluorescent images of the cells were photographed under the same conditions, the frequency distribution of fluorescence intensity relative to pixels within the same area was calculated using image analyzing software included with the microscope, and the fluorescence sum (i.e., a=sum; fluorescence intensity×pixel number) was determined.

<Electrophoresis and Immunoblot Analysis of Seed Protein>

20 seed grains were pulverized in 40 µl of SDS sample buffer, and the supernatant resulting from centrifugation was designated as a seed protein sample. In accordance with a conventional technique, 15 µl of the sample was subjected to SDS polyacrylamide electrophoresis. The electrophoresed gel was stained with a solution of 0.2% Coomassie brilliant blue R-250 (containing 25% methanol and 10% acetic acid).

Immunoblot analysis was carried out by subjecting 5 µl of the sample to SDS polyacrylamide gel electrophoresis and transferring the proteins in the gel onto a nitrocellulose membrane via semi-dry blotting. Detection of the proteins that had been transferred onto the nitrocellulose membrane with the use of an anti-protein antibody was carried out in accordance with the protocols of GE Healthcare Bio-Sciences using ECL Western blotting detection reagents. In this case, 1/5000-fold diluted antibodies were used as the primary antibodies (the anti-oleosin antibodies or the anti-GFP antibodies) and the secondary antibodies. Luminescence was detected using a luminescent image analyzer (LAS-1000 plus, Fujifilm Corporation).

<Electron Microscopic Seed Cell Observation>

Half seeds were immobilized using a fixative (4% paraformaldehyde, 1% glutaraldehyde, 10% DMSO, 0.05M cacodylate buffer (pH 7.4)). The immobilized sample was embedded in epon 812 resin and ultrathin sections were prepared using a Leica Microtome Ultracut UCT. The ultrathin sections were subjected to electron staining with 4% uranium acetate and 0.4% lead citrate and then observed under an electron microscope (H-7600, Hitachi, Ltd.).

<Measurement of Oil-and-Fat Amount in Seed>

While performing neutralization of static electricity, the seeds were weighed with an accurate electron balance using drug packing paper, and 10 to 12 mg of seeds were fractionated. The seeds were introduced into a test tube for pulsed NMR, and the oil-and-fat content in seeds (% by weight) was determined using a MARAN-23 pulsed NMR (Resonance Instruments) based on the $^1$H-pulsed NMR relaxation times. The detailed measurement procedure described in the instructions for pulsed-NMR measurements was employed.

<Analysis of Fatty Acid Composition in Seed Oil-and-Fat>

About 1 mg to 5 mg of seed samples were fractionated and introduced into a 1.5-ml micro test tube. A tungsten carbide bead ($\phi$=3 mm) was added to the micro test tube, and 450 µl of methanol, 50 µl of a solution of butyl hydroxyl toluene mixed with a methanol solvent at 0.2% (w/v), and 10 µl of 0.2% C15:0 fatty acid as an internal standard material were further added. The micro test tube to which such various reagents and the sample had been added was subjected to oscillation at a frequency of 1/20 s using a Retsch Mixer Mill Type MM301 for 1 minute, and the seeds were pulverized. The sample was transferred to a 10-ml test tube with a screw cap. Further, the inside of the micro test tube was washed twice with 250 µl of methanol, and the methanol wash solution was added to the test tube to adjust the amount of the sample solution to about 1 ml. A 10% hydrochloric acid/methanol solution (1 ml) was added thereto, the mixture was treated at 80° C. for 1 hour, 1.5 ml of n-hexane was added thereto, the mixture was agitated using a vortex mixer, and the n-hexane layer was transferred to a 10-ml spit tube. Further, the inside of the test tube used for methanolysis was washed with 1 ml of n-hexane, and the n-hexane-washed layer was added to the spit tube. The resulting n-hexane solvent solution was subjected to nitrogen gas purging at 40° C., and fatty acid methyl ester was dried. The dried fatty acid methyl ester was dissolved in 500 µl of n-hexane, and various fatty acid methyl esters were separated and quantified via GC-FID. Quantification was carried out with reference to the area of the internal standard (C15:0 fatty acid).

Results and Discussion

<Establishment of Method for Screening for Mutant that is Deficient in Oil Body Formation>

Figure 1:
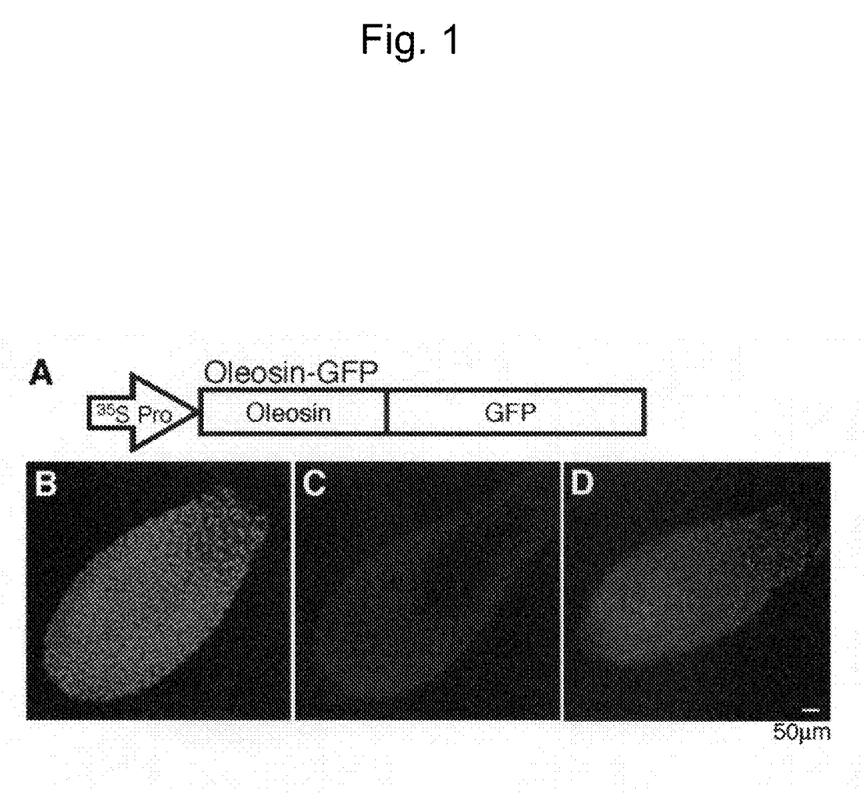

The fusion gene (oleosin-GFP) encoding the fusion protein of oleosin and green fluorescent protein (GFP) was prepared and then ligated to a site downstream of DNA of the 35S promoter of the cauliflower mosaic virus (FIG. 1A). The DNA construct was introduced into genome DNA of *Arabidopsis thaliana* by the *Agrobacterium* method to prepare a transgenic *Arabidopsis thaliana* plant, and the resultant was designated as oleG. The results of observation of oleG cotyledons, which had been germinated in the dark for 6 days, using a fluorescent microscope are shown in FIG. 1B. As is apparent from FIG. 1B, an oil body membrane is labeled with GFP fluorescence, and aggregates of many small oil bodies are present. Further, the presence of oil bodies in germs and green cotyledons, true leaves, and petals, which had been germinated under light, was observed, in addition to cotyledons, which had been germinated in the dark.

In order to identify the gene associated with the mechanism for accumulating plant oil-and-fats in oil bodies, the oleG seeds were subjected to mutation with ethyl methane sulfonate to obtain progeny M2 seeds. The M2 plants, which had been germinated in the dark for 6 days, were observed under a fluorescent microscope, and mutant A (FIG. 1C) and mutant B (FIG. 1D) exhibiting fluorescent intensity different from that of oleG were obtained. The GFP fluorescent intensity in the germinated cotyledons of such mutants was lower than that of oleG.

<Correlation Between Sum of GFP Fluorescence and Oil-and-Fat Content in Seed>

Confocal laser microscope photographs of GFP fluorescence of cotyledons of OleG, mutant A, and mutant B, which had been germinated in the dark for 6 days, under the same conditions in the same area with the same pixel number were obtained, and the sum of GFP fluorescence (i.e., a=sum; fluorescence intensity×pixel number) was determined based on the frequency distribution of the pixel number relative to the GFP fluorescence intensity of each photograph. When the sum of OleG fluorescence was designated as 100%, the fluorescence sum of mutant A was 37.9%, and that of mutant B was 85.1%. Separately, the oil-and-fat contents in seeds (mean±standard deviation) of OleG, mutant A, and mutant B were measured and found to be 34.66%±0.43%, 26.91%±0.34%, and 32.34%±0.49%, respectively.

Figure 2:
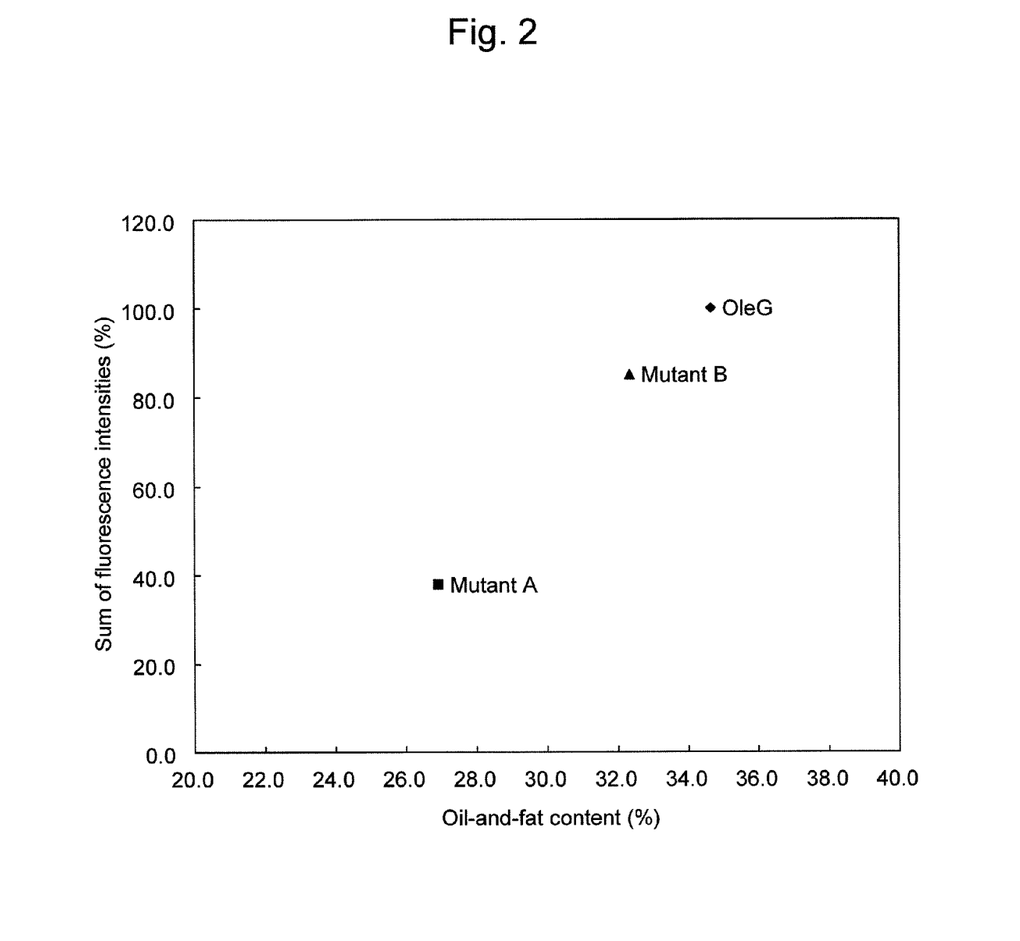
FIG. 2 is a characteristic diagram showing the correlation of the sum of GFP fluorescence (%) and the oil-and-fat content in a seed.

Based on the results, the correlation between the sum of GFP fluorescence intensities and the oil-and-fat content in a seed are shown in FIG. 2 and Table 1.

TABLE 1

| Label | oleG etiolated cotyledon OleG | oleGE11-6 etiolated cotyledon Mutant A | oleGE7-6 etiolated cotyledon Mutant B |
|---|---|---|---|
| Oil-and-fat content in seed (%) | 34.7 | 26.9 | 32.3 |
| Sum of fluorescence intensities of image (a) | 5,817,997.0 | 2,205,550.0 | 4,951,861.0 |
| Sum of fluorescence (%) when oleG etiolated cotyledon is 100% | 100.0 | 37.9 | 85.1 |

As shown in FIG. 2 and Table 1, it was found that the sum of fluorescence intensities in a cotyledon resulting from the oleosin-GFP fusion protein was correlated with the oil-and-fat content in a seed that was measured in a nondestructive manner ($y=8.1331x-180.25$, $R^2=0.9959$). The results attained in the examples demonstrate that measurement of fluorescence intensities in a cotyledon of a transgenic plant in which the oleosin-GFP fusion protein is expressed leads to easy evaluation of the oil-and-fat content in a seed.

INDUSTRIAL APPLICABILITY

The present invention can provide a method for evaluating the oil-and-fat amount in a seed in a nondestructive manner only by performing measurement with visible light that can be carried out in a simple manner and that can quantitatively measure large quantities of samples at a time. The present invention can also provide a method for screening for a plant species, a plant variety, or a mutant plant exhibiting a varied level of oil-and-fat amount in a seed only by performing measurement with visible light that can be carried out in a simple manner and that can quantitatively measure large quantities of samples at a time. The evaluation method and the screening method of the present invention are very simple since such methods can evaluate the oil-and-fat amount in a seed or genetic changes thereof in a nondestructive manner. The oil-and-fat amount in a seed is a genetic and quantitative character, and a method that can quantitatively measure large quantities of such oil-and-fat amount in a simple manner is industrially advantageous.

All publications, patents, and patent applications cited herein are incorporated herein by reference in their entirety.

---

The invention claimed is:

1. A method for evaluating the oil-and-fat amount in a seed comprising a step of measuring the visible light intensity in a cotyledon of a plant that expresses a fusion protein of a protein that has oil body specificity and a protein that can be detected by visible light and a step of evaluating the oil-and-fat content in a seed based on the visible light intensity measured in the former step.

2. The method for evaluation according to claim 1, wherein the protein that has oil body specificity is a protein selected from the group consisting of oleosin, steroleosin, and caleosin.

3. The method for evaluation according to claim 1, wherein the protein that has oil body specificity is oleosin.

4. The method for evaluation according to claim 1, wherein the protein that can be detected by visible light is green fluorescent protein (GFP).

5. The method for evaluation according to claim 1, wherein the step of evaluating the oil-and-fat content comprises calculating the sum of visible light intensities in a cotyledon and conducting an evaluation based on a positive correlation between the sum and the oil-and-fat content in a seed.

6. The method for evaluation according to claim 5, which further comprises a step of evaluating the positive correlation between the sum of visible light intensities and the oil-and-fat content in a seed based on measured values obtained via a measurement of the sum of visible light intensities and quantification of the oil-and-fat content in unpulverized seeds using pulsed NMR.

7. The method for evaluation according to claim 6, wherein the measurement of the sum of visible light intensities is carried out with the use of a fluorescence microscope, a fluorospectrophotometer, a fluorescent titer plate reader, or a fluorescent image analyzer.

8. The method for evaluation according to claim 1, wherein the plant is obtained from a plant cell or a cultured plant cell that has been subjected to mutagen treatment.

9. The method for evaluation according to claim 1, wherein the plant is an oil plant.

10. The method for evaluation according to claim 1, wherein the plant is a dicotyledonous plant.

11. The method for evaluation according to claim 1, wherein the plant belongs to the genus Brassicaceae.

12. The method for evaluation according to claim 1, wherein the plant is *Arabidopsis thaliana*.

13. The method for evaluation according to claim 1, wherein the visible light intensities are measured with the use of a fluorescent microscope, a fluorospectrophotometer, a fluorescent titer plate reader, or a fluorescent image analyzer.

14. A method of screening a plant species, a plant variety, or a mutant plant exhibiting a varied level of oil-and-fat content in a seed comprising a step of measuring visible light intensities in a cotyledon of a plant cell, a cultured plant cell, or a plant that expresses a fusion protein of a protein that has oil body specificity and a protein that can be detected by visible light.

15. The method for screening according to claim 14, wherein the protein that has oil body specificity is a protein selected from the group consisting of oleosin, steroleosin, and caleosin.

16. The method for screening according to claim 14, wherein the protein that has oil body specificity is oleosin.

17. The method for screening according to claim 14, wherein the protein that can be detected by visible light is green fluorescent protein (GFP).

18. A method for screening for a plant exhibiting a varied level of oil-and-fat content comprising a step of subjecting a plant cell, a cultured plant cell, or a plant expressing a fusion protein of a protein that has oil body specificity and a protein that can be detected by visible light to mutagen treatment, a step of measuring visible light intensities in a cotyledon after the step of mutagen treatment, and a step of evaluating changes in the oil-and-fat content in a seed resulting from the mutagen treatment based on the visible light intensities measured in the above step.

19. The method for screening according to claim 18, wherein the protein that has oil body specificity is a protein selected from the group consisting of oleosin, steroleosin, and caleosin.

20. The method for screening according to claim 18, wherein the protein that has oil body specificity is oleosin.

21. The method for screening according to claim 18, wherein the protein that can be detected by visible light is green fluorescent protein (GFP).

22. The method for screening according to claim 19, wherein the step of evaluating changes in the oil-and-fat content comprises calculating the sum of visible light intensities in a cotyledon and conducting an evaluation based on a positive correlation between the sum and the oil-and-fat content in a seed.

23. The method for screening according to claim 22, which further comprises a step of evaluating the positive correlation between the sum of visible light intensities and the oil-and-fat content in a seed based on measured values obtained via a measurement of the sum of visible light intensities and quantification of the oil-and-fat content in unpulverized seeds using pulsed NMR.

24. The method for screening according to claim 23, wherein the measurement of the sum of visible light intensities is carried out with the use of a fluorescence microscope, a fluorospectrophotometer, a fluorescent titer plate reader, or a fluorescent image analyzer.

25. The method for screening according to claim 18, wherein the plant is an oil plant.

26. The method for screening according to claim 18, wherein the plant is a dicotyledonous plant.

27. The method for screening according to claim 18, wherein the plant belongs to the genus Brassicaceae.

28. The method for screening according to claim 18, wherein the plant is *Arabidopsis thaliana*.

29. The method for screening according to claim 18, wherein the visible light intensities are measured with the use of a fluorescent microscope, a fluorospectrophotometer, a fluorescent titer plate reader, or a fluorescent image analyzer.

* * * * *

SEQUENCE LISTING

```
<160> NUMBER OF SEQ ID NOS: 8

<210> SEQ ID NO 1
<211> LENGTH: 1239
<212> TYPE: DNA
<213> ORGANISM: Artificial
<220> FEATURE:
<223> OTHER INFORMATION: Synthetic DNA coding an Oleosin-GFP fusion gene
<220> FEATURE:
<221> NAME/KEY: CDS
<222> LOCATION: (1)..(1239)

<400> SEQUENCE: 1 atg gcg gat aca gct aga gga acc cat cac gat atc atc ggc aga gac        48
Met Ala Asp Thr Ala Arg Gly Thr His His Asp Ile Ile Gly Arg Asp
1               5                   10                  15 cag tac ccg atg atg ggc cga gac cga gac cag tac cag atg tcc gga        96
Gln Tyr Pro Met Met Gly Arg Asp Arg Asp Gln Tyr Gln Met Ser Gly
                20                  25                  30 cga gga tct gac tac tcc aag tct agg cag att gct aaa gct gca act       144
Arg Gly Ser Asp Tyr Ser Lys Ser Arg Gln Ile Ala Lys Ala Ala Thr
            35                  40                  45 gct gtc aca gct ggt ggt tcc ctc ctt gtt ctc tcc agc ctt acc ctt       192
Ala Val Thr Ala Gly Gly Ser Leu Leu Val Leu Ser Ser Leu Thr Leu
        50                  55                  60 gtt gga act gtc ata gct ttg act gtt gca aca cct ctg ctc gtt atc       240
Val Gly Thr Val Ile Ala Leu Thr Val Ala Thr Pro Leu Leu Val Ile
65                  70                  75                  80 ttc agc cca atc ctt gtc ccg gct ctc atc aca gtt gca ctc ctc atc       288
Phe Ser Pro Ile Leu Val Pro Ala Leu Ile Thr Val Ala Leu Leu Ile
                85                  90                  95 acc ggt ttt ctt tcc tct gga ggg ttt ggc att gcc gct ata acc gtt       336
Thr Gly Phe Leu Ser Ser Gly Gly Phe Gly Ile Ala Ala Ile Thr Val
                100                 105                 110 ttc tct tgg att tac aag tac gca acg gga gag cac cca cag gga tca       384
```

```
                Phe Ser Trp Ile Tyr Lys Tyr Ala Thr Gly Glu His Pro Gln Gly Ser
                    115                 120                 125 gac aag ttg gac agt gca agg atg aag ttg gga agc aaa gct cag gat              432
Asp Lys Leu Asp Ser Ala Arg Met Lys Leu Gly Ser Lys Ala Gln Asp
            130                 135                 140 ctg aaa gac aga gct cag tac tac gga cag caa cat act ggt ggg gaa              480
Leu Lys Asp Arg Ala Gln Tyr Tyr Gly Gln Gln His Thr Gly Gly Glu
145                 150                 155                 160 cat gac cgt gac cgt act cgt ggt ggc cag cac act act atg gtg agc              528
His Asp Arg Asp Arg Thr Arg Gly Gly Gln His Thr Thr Met Val Ser
                165                 170                 175 aag ggc gag gag ctg ttc acc ggg gtg gtg ccc atc ctg gtc gag ctg              576
Lys Gly Glu Glu Leu Phe Thr Gly Val Val Pro Ile Leu Val Glu Leu
            180                 185                 190 gac ggc gac gtg aac ggc cac aag ttc agc gtg tcc ggc gag ggc gag              624
Asp Gly Asp Val Asn Gly His Lys Phe Ser Val Ser Gly Glu Gly Glu
        195                 200                 205 ggc gat gcc acc tac ggc aag ctg acc ctg aag ttc atc tgc acc acc              672
Gly Asp Ala Thr Tyr Gly Lys Leu Thr Leu Lys Phe Ile Cys Thr Thr
210                 215                 220 ggc aag ctg ccc gtg ccc tgg ccc acc ctc gtg acc acc ttc acc tac              720
Gly Lys Leu Pro Val Pro Trp Pro Thr Leu Val Thr Thr Phe Thr Tyr
225                 230                 235                 240 ggc gtg cag tgc ttc agc cgc tac ccc gac cac atg aag cag cac gac              768
Gly Val Gln Cys Phe Ser Arg Tyr Pro Asp His Met Lys Gln His Asp
                245                 250                 255 ttc ttc aag tcc gcc atg ccc gaa ggc tac gtc cag gag cgc acc atc              816
Phe Phe Lys Ser Ala Met Pro Glu Gly Tyr Val Gln Glu Arg Thr Ile
            260                 265                 270 ttc ttc aag gac gac ggc aac tac aag acc cgc gcc gag gtg aag ttc              864
Phe Phe Lys Asp Asp Gly Asn Tyr Lys Thr Arg Ala Glu Val Lys Phe
        275                 280                 285 gag ggc gac acc ctg gtg aac cgc atc gag ctg aag ggc atc gac ttc              912
Glu Gly Asp Thr Leu Val Asn Arg Ile Glu Leu Lys Gly Ile Asp Phe
290                 295                 300 aag gag gac ggc aac atc ctg ggg cac aag ctg gag tac aac tac aac              960
Lys Glu Asp Gly Asn Ile Leu Gly His Lys Leu Glu Tyr Asn Tyr Asn
305                 310                 315                 320 agc cac aac gtc tat atc atg gcc gac aag cag aag aac ggc atc aag              1008
Ser His Asn Val Tyr Ile Met Ala Asp Lys Gln Lys Asn Gly Ile Lys
                325                 330                 335 gtg aac ttc aag atc cgc cac aac atc gag gac ggc agc gtg cag ctc              1056
Val Asn Phe Lys Ile Arg His Asn Ile Glu Asp Gly Ser Val Gln Leu
            340                 345                 350 gcc gac cac tac cag cag aac acc ccc atc ggc gac ggc ccc gtg ctg              1104
Ala Asp His Tyr Gln Gln Asn Thr Pro Ile Gly Asp Gly Pro Val Leu
        355                 360                 365 ctg ccc gac aac cac tac ctg agc acc cag tcc gcc ctg agc aaa gac              1152
Leu Pro Asp Asn His Tyr Leu Ser Thr Gln Ser Ala Leu Ser Lys Asp
370                 375                 380 ccc aac gag aag cgc gat cac atg gtc ctg ctg gag ttc gtg acc gcc              1200
Pro Asn Glu Lys Arg Asp His Met Val Leu Leu Glu Phe Val Thr Ala
385                 390                 395                 400 gcc ggg atc act cac ggc atg gac gag ctg tac aag taa                          1239
Ala Gly Ile Thr His Gly Met Asp Glu Leu Tyr Lys
                405                 410

<210> SEQ ID NO 2
<211> LENGTH: 412
<212> TYPE: PRT
<213> ORGANISM: Artificial
```

<220> FEATURE:
<223> OTHER INFORMATION: Synthetic Construct

<400> SEQUENCE: 2

```
Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys Tyr Ala Thr Gly Glu His Pro Gln Gly Ser
        115                 120                 125

Asp Lys Leu Asp Ser Ala Arg Met Lys Leu Gly Ser Lys Ala Gln Asp
    130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr Met Val Ser
                165                 170                 175

Lys Gly Glu Glu Leu Phe Thr Gly Val Val Pro Ile Leu Val Glu Leu
            180                 185                 190

Asp Gly Asp Val Asn Gly His Lys Phe Ser Val Ser Gly Glu Gly Glu
        195                 200                 205

Gly Asp Ala Thr Tyr Gly Lys Leu Thr Leu Lys Phe Ile Cys Thr Thr
    210                 215                 220

Gly Lys Leu Pro Val Pro Trp Pro Thr Leu Val Thr Thr Phe Thr Tyr
225                 230                 235                 240

Gly Val Gln Cys Phe Ser Arg Tyr Pro Asp His Met Lys Gln His Asp
                245                 250                 255

Phe Phe Lys Ser Ala Met Pro Glu Gly Tyr Val Gln Glu Arg Thr Ile
            260                 265                 270

Phe Phe Lys Asp Asp Gly Asn Tyr Lys Thr Arg Ala Glu Val Lys Phe
        275                 280                 285

Glu Gly Asp Thr Leu Val Asn Arg Ile Glu Leu Lys Gly Ile Asp Phe
    290                 295                 300

Lys Glu Asp Gly Asn Ile Leu Gly His Lys Leu Glu Tyr Asn Tyr Asn
305                 310                 315                 320

Ser His Asn Val Tyr Ile Met Ala Asp Lys Gln Lys Asn Gly Ile Lys
                325                 330                 335

Val Asn Phe Lys Ile Arg His Asn Ile Glu Asp Gly Ser Val Gln Leu
            340                 345                 350

Ala Asp His Tyr Gln Gln Asn Thr Pro Ile Gly Asp Gly Pro Val Leu
        355                 360                 365

Leu Pro Asp Asn His Tyr Leu Ser Thr Gln Ser Ala Leu Ser Lys Asp
    370                 375                 380

Pro Asn Glu Lys Arg Asp His Met Val Leu Leu Glu Phe Val Thr Ala
385                 390                 395                 400
```

Ala Gly Ile Thr His Gly Met Asp Glu Leu Tyr Lys
            405                 410

<210> SEQ ID NO 3
<211> LENGTH: 35
<212> TYPE: DNA
<213> ORGANISM: Artificial
<220> FEATURE:
<223> OTHER INFORMATION: Synthetic DNA

<400> SEQUENCE: 3
aaaaagcagg ctcaatggcg gatacagcta gagga        35

<210> SEQ ID NO 4
<211> LENGTH: 36
<212> TYPE: DNA
<213> ORGANISM: Artificial
<220> FEATURE:
<223> OTHER INFORMATION: Synthetic DNA

<400> SEQUENCE: 4
ctcgcccttg ctcaccatag tagtgtgctg gccacc        36

<210> SEQ ID NO 5
<211> LENGTH: 36
<212> TYPE: DNA
<213> ORGANISM: Artificial
<220> FEATURE:
<223> OTHER INFORMATION: Synthetic DNA

<400> SEQUENCE: 5
ggtggccagc acactactat ggtgagcaag ggcgag        36

<210> SEQ ID NO 6
<211> LENGTH: 34
<212> TYPE: DNA
<213> ORGANISM: Artificial
<220> FEATURE:
<223> OTHER INFORMATION: Synthetic DNA

<400> SEQUENCE: 6
agaaagctgg gtcttacttg tacagctcgt ccat        34

<210> SEQ ID NO 7
<211> LENGTH: 29
<212> TYPE: DNA
<213> ORGANISM: Artificial
<220> FEATURE:
<223> OTHER INFORMATION: Synthetic DNA

<400> SEQUENCE: 7
ggggacaagt ttgtacaaaa aagcaggct        29

<210> SEQ ID NO 8
<211> LENGTH: 28
<212> TYPE: DNA
<213> ORGANISM: Artificial
<220> FEATURE:
<223> OTHER INFORMATION: Synthetic DNA

<400> SEQUENCE: 8
ggggaccact ttgtacaaga aagctggg        28